(12) United States Patent
Choi et al.

(10) Patent No.: US 11,482,125 B2
(45) Date of Patent: Oct. 25, 2022

(54) METHOD AND APPARATUS FOR PROVIDING TOOTH-BRUSHING GUIDE INFORMATION USING AUGMENTED REALITY

(71) Applicant: KITTEN PLANET CO., LTD., Gyeonggi-do (KR)

(72) Inventors: Jong Ho Choi, Gyeonggi-do (KR); Sung Jin Park, Gyeonggi-do (KR); Dong Jun Lee, Gyeonggi-do (KR); Jee Yun Lee, Jongno-gu (KR)

(73) Assignee: KITTEN PLANET CO., LTD., Gyeonggi-do (KR)

( * ) Notice: Subject to any disclaimer, the term of this patent is extended or adjusted under 35 U.S.C. 154(b) by 111 days.

(21) Appl. No.: 16/086,283

(22) PCT Filed: Oct. 20, 2017

(86) PCT No.: PCT/KR2017/011695
§ 371 (c)(1),
(2) Date: Sep. 18, 2018

(87) PCT Pub. No.: WO2019/022302
PCT Pub. Date: Jan. 31, 2019

(65) Prior Publication Data
US 2021/0201687 A1    Jul. 1, 2021

(30) Foreign Application Priority Data
Jul. 27, 2017 (KR) .......... 10-2017-0095670

(51) Int. Cl.
*G09B 5/02* (2006.01)
*G16H 20/30* (2018.01)
(Continued)

(52) U.S. Cl.
CPC ............ *G09B 5/02* (2013.01); *A61B 5/4547* (2013.01); *A61C 9/0046* (2013.01); *A61C 17/00* (2013.01);
(Continued)

(58) Field of Classification Search
CPC .... G09B 5/02; G09B 19/0084; G09B 23/283; G16H 20/30; G16H 30/20; G16H 30/40;
(Continued)

(56) References Cited

U.S. PATENT DOCUMENTS

2010/0170052 A1* 7/2010 Ortins ................ A63F 13/213
                                                                        15/106
2011/0010226 A1   1/2011 Guild
2017/0238692 A1*  8/2017 Sarubbo ............. A46B 15/0085

FOREIGN PATENT DOCUMENTS

JP     2004283594 A   10/2004
KR     20120013369 A   2/2012
(Continued)

OTHER PUBLICATIONS

Unknown, "Virtual and augmented reality simulation of a dental treatment system", Article, The Sun, published Mar. 22, 2017, http://it.chosun.com/site/data/html_dir/2017/03/22/2017032285011.html, last accessed Jul. 17, 2018, 3 pages.

(Continued)

*Primary Examiner* — Robert P Bullington
(74) *Attorney, Agent, or Firm* — SoCal IP Law Group LLP; Mark Andrew Goldstein

(57) ABSTRACT

A method of providing tooth-brushing guide information according to an embodiment of the present invention includes an operation in which a user terminal analyzes a captured image of a user, recognizes the face of the user, and identifies landmarks of the face; an operation in which the user terminal generates a personalized dental model of the (Continued)

user using the landmarks, an operation in which the user terminal provides a virtual dental image by augmented reality using the dental model; and an operation in which the user terminal provides tooth-brushing guide information using the dental model.

17 Claims, 20 Drawing Sheets

(51) Int. Cl.
    *G16H 30/20* (2018.01)
    *G16H 30/40* (2018.01)
    *G16H 40/60* (2018.01)
    *G06Q 50/22* (2018.01)
    *A61C 17/00* (2006.01)
    *A61C 9/00* (2006.01)
    *A61B 5/00* (2006.01)
    *G09B 19/00* (2006.01)
    *G06V 20/20* (2022.01)
    *A61B 34/10* (2016.01)
    *G09B 23/28* (2006.01)

(52) U.S. Cl.
    CPC ............. *G06Q 50/22* (2013.01); *G06V 20/20* (2022.01); *G09B 19/0084* (2013.01); *G16H 20/30* (2018.01); *G16H 30/20* (2018.01); *G16H 30/40* (2018.01); *G16H 40/60* (2018.01); *A61B 2034/105* (2016.02); *G09B 23/283* (2013.01)

(58) Field of Classification Search
    CPC   G16H 40/60; A61B 5/4547; A61B 2034/105; A61C 9/0046; A61C 17/00; G06K 9/00671; G06Q 50/22
    USPC .......................................................... 434/350
    See application file for complete search history.

(56) References Cited

FOREIGN PATENT DOCUMENTS

| | | |
|---|---|---|
| KR | 1020120010875 A | 2/2012 |
| KR | 101565516 B1 | 11/2015 |
| KR | 20160083449 A | 7/2016 |
| KR | 20160103468 A | 9/2016 |
| WO | 2016020803 A1 | 2/2016 |

OTHER PUBLICATIONS

Korean Intellectual Property Office, Office Action for Korean Application No. 10-2017-0095670, dated Sep. 17, 2018, 10 total pages.
Korean Intellectual Property Office, Office for Application No. 2020-514477, dated Nov. 17, 2020, 3 total pages.
Korean Intellectual Property Office, Notice of Allowance for Application No. 120170210283, dated May 20, 2019, 2 total pages.

* cited by examiner

FIG. 8a

|  |  | ERUPTION TIME OF DECIDUOUS TEETH (MONTH) | FALL-OUT TIME OF DECIDUOUS TEETH (AGE) |
|---|---|---|---|
| MAXILLA | FIRST FRONT TEETH | 7-8 | 6-7 |
|  | SECOND FRONT TEETH | 8-9 | 7-8 |
|  | CANINE TEETH | 16-20 | 10-12 |
|  | FIRST BACK TEETH | 12-16 | 9-11 |
|  | SECOND BACK TEETH | 20-30 | 10-12 |
| MANDIBLE | FIRST FRONT TEETH | 6-7 | 6-7 |
|  | SECOND FRONT TEETH | 6-7 | 7-8 |
|  | CANINE TEETH | 16-20 | 9-12 |
|  | FIRST BACK TEETH | 12-16 | 9-11 |
|  | SECOND BACK TEETH | 20-30 | 10-12 |

FIG. 8b

|  | MAXILLARY (AGE) | MANDIBULAR (AGE) |
|---|---|---|
| FIRST FRONT TEETH | 7-8 | 6-7 |
| SECOND FRONT TEETH | 8-9 | 7-8 |
| CANINE TEETH | 16-20 | 10-12 |
| FIRST SMALL BACK TEETH | 12-16 | 9-11 |
| SECOND SMALL BACK TEETH | 20-30 | 10-12 |
| FIRST LARGE BACK TEETH | 6-7 | 6-7 |
| SECOND LARGE BACK TEETH | 6-7 | 7-8 |
| THIRD LARGE BACK TEETH | 16-20 | 9-12 |

240

METHOD AND APPARATUS FOR PROVIDING TOOTH-BRUSHING GUIDE INFORMATION USING AUGMENTED REALITY

RELATED APPLICATION INFORMATION

This application claims priority from International PCT Application No. PCT/KR2017/011695 filed Oct. 10, 2017, which claims priority from Korean Patent Application No. 10-2017-0095670, filed on Jul. 27, 2017 in the Korean Intellectual Property Office, the disclosures of which are incorporated herein in their entirety by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

The present invention relates to a method of providing tooth-brushing guide information using augmented reality and an apparatus therefor, and more particularly, to a method of providing guide information related to tooth-brushing, e.g., guide information such as a degree to which tooth-brushing is performed on each area, by using augmented reality, and an apparatus for performing the method.

Most children hate brushing their teeth. However, teeth are body parts that are not regenerated, and thus, when a permanent tooth is damaged, other medical assistance is required. Furthermore, children hate seeing the dentist much more than brushing their teeth. Therefore, proper tooth care is extremely important.

To this end, it is important to make children form proper tooth-brushing habits from the time when deciduous teeth begin to erupt. Tooth-brushing is one of healthy life habits for maintaining a healthy life. In reality, one can keep teeth clean just by perfectly brushing one's teeth. The reason why children's teeth rot even if they brush teeth once or more every day is due to improper tooth-brushing habits.

To solve such a problem, there is a method in which information related to proper tooth brushing is provided through a video or the like. However, the method merely plays designated content without an interaction with a child, who is a user. Thus, children's level of concentration easily decreases while the children watch content, and children become careless about tooth-brushing.

Therefore, in addition to providing children with content related to proper tooth-brushing habits, a method of providing intercommunication type guide information to children so that the children are able to concentrate on the content is required.

Technical Problem

One aspect of the present invention provides a method of providing tooth-brushing guide information using augmented reality and an apparatus therefor.

Aspects of the present invention are not limited to that mentioned above, and other unmentioned aspects should be clearly understood by those of ordinary skill in the art to which the present invention pertains from the description below.

Technical Solution

A method of providing tooth-brushing guide information according to an embodiment of the present invention for solving the above aspects includes an operation in which a user terminal analyzes a captured image of a user, recognizes the face of the user, and identifies landmarks of the face; an operation in which the user terminal generates a personalized dental model of the user using the landmarks, an operation in which the user terminal provides a virtual dental image by augmented reality using the dental model; and an operation in which the user terminal provides tooth-brushing guide information using the dental model.

Preferably, the identifying of the landmarks of the face may include identifying one or more of an eyebrow, an eye, a nose, both cheeks, a mouth, an ear, and a jawline of the user as the landmarks.

Preferably, the generating of the personalized dental model of the user may include estimating one or more of the position, size, and arrangement of teeth of the user using the landmarks.

Preferably, the estimating of one or more of the position, size, and arrangement of the teeth of the user may include estimating that mandibular right back teeth are located at a midpoint portion between a position at which the jawline and the right ear of the user meet and a position of the center of the mouth of the user, estimating that mandibular left back teeth are located at a midpoint portion between a position at which the jawline and the left ear of the user meet and the position of the center of the mouth of the user, and estimating that front teeth are located at the position of the center of the mouth of the user.

Preferably, the estimating of one or more of the position, size, and arrangement of the teeth of the user may include estimating the size of the jaw of the user from the jawline of the user, and estimating the size of the teeth of the user using the estimated size of the jaw.

Preferably, the estimating of one or more of the position, size, and arrangement of the teeth of the user may include estimating the shape of the jaw of the user from the jawline of the user and estimating the arrangement of the teeth of the user as any one of a square arch, an oval arch, and a triangular arch using the estimated shape of the jaw.

Preferably, the generating of the personalized dental model of the user may include receiving personalized information including one or more of the date of birth, gender, height, weight, number of teeth, position of teeth, number of decayed teeth, and position of decayed teeth from the user, and modifying the personalized dental model of the user using the received personalized information.

Preferably, the modifying of the personalized dental model of the user may include counting back the number of months and number of years from the date of birth of the user and determining whether the teeth of the user are permanent teeth on the basis of the counted number of months and number of years, and limiting the number of teeth included in the dental model to 20 or less when the teeth of the user are deciduous teeth and to 28 or less when the teeth of the user are permanent teeth.

Preferably, the modifying of the personalized dental model of the user may include counting back the number of months and number of years from the date of birth of the user and determining whether the teeth of the user are permanent teeth on the basis of the counted number of months and number of years, and modifying one or more of the size and shape of the teeth included in the dental model according to a result of determining whether the teeth of the user are permanent teeth.

Preferably, the modifying of the personalized dental model of the user may include modifying one or more of the number, size, and shape of the teeth included in the dental model using one or more of the gender, height, age, and weight of the user.

Preferably, the providing of the virtual dental image by augmented reality may include, when a first tooth has not yet erupted or has fallen out in the dental model, not displaying a tooth at a position corresponding to the first tooth in the virtual dental image.

Preferably, the providing of the virtual dental image by augmented reality may include further providing a virtual toothbrush image by augmented reality or providing only the virtual toothbrush image instead of providing the virtual dental image.

Preferably, the further providing of the virtual toothbrush image by augmented reality or providing of only the virtual toothbrush image instead of providing the virtual dental image may include analyzing the captured image and estimating a hand of the user with which a toothbrush is held and an angle thereof, and displaying the position and angle of the virtual toothbrush image by augmented reality on the basis of the estimated hand and angle thereof.

Preferably, the providing of the tooth-brushing guide information may include dividing the dental model into a predetermined number of parts and displaying a degree to which tooth-brushing is performed on each part using colors.

Preferably, the displaying of the degree to which tooth-brushing is performed on each part using colors may include, when the teeth of the user are deciduous teeth, dividing the dental model into a total of eight parts including front and back surfaces of maxillary left teeth, front and back surfaces of mandibular left teeth, front and back surfaces of maxillary right teeth, and front and back surfaces of mandibular right teeth.

Preferably, the displaying of the degree to which tooth-brushing is performed on each part using colors may include, when the teeth of the user are permanent teeth, dividing the dental model into a total of sixteen parts including front, top, and back surfaces of maxillary left back teeth, front, top, and back surfaces of mandibular left back teeth, front and back surfaces of maxillary front teeth, front and back surfaces of mandibular front teeth, front, top, and back surfaces of maxillary right back teeth, and front, top, and back surfaces of mandibular right back teeth.

Preferably, the providing of the tooth-brushing guide information may include dividing the dental model into a predetermined number of parts and visually or aurally guiding one or more of the number of required tooth-brushing strokes, a direction of tooth-brushing, and duration of tooth-brushing for each part.

Preferably, the visually or aurally guiding of one or more of the number of required tooth-brushing strokes, the direction of tooth-brushing, and the duration of tooth-brushing for each part may include, when a first tooth has not yet erupted or has fallen out in the dental model, not guiding for a position corresponding to the first tooth.

Preferably, the visually or aurally guiding of one or more of the number of required tooth-brushing strokes, the direction of tooth-brushing, and the duration of tooth-brushing for each part may include guiding horizontal tooth-brushing using a roll technique or a Fones technique when the user is younger than a predetermined age and guiding vertical tooth-brushing using a Bass technique or a modified Bass technique in other cases.

A computer program according to another embodiment of the present invention for solving the above aspects is a computer program that is mapped to hardware and stored in a computer readable medium to execute a method of providing tooth-brushing guide information according to the present invention.

A method of providing content using augmented reality according to still another embodiment of the present invention for solving the above aspects includes an operation in which a content providing apparatus analyzes a captured image of a user, recognizes a first portion of the user, and identifies a landmark of the first portion; an operation in which the content providing apparatus generates a personalized first portion model of the user using the landmark; an operation in which the content providing apparatus provides a virtual first portion image by augmented reality using the first portion model; and an operation in which the content providing apparatus provides content related to the first portion using the first portion model.

Advantageous Effects

Advantageous effects of the present invention are as follows.

According to the present invention, since tooth-brushing guide information is provided using augmented reality, children can concentrate better on the provided content. Particularly, since guide information is provided through interactions with children instead of fixed content merely being played to the children, it is possible to keep the children interested in the provided content.

Further, since content customized for each individual can be provided when providing content through augmented reality, it is possible to arouse more interest in the provided content. In this way, tooth-brushing may be considered as a game by children, and it is possible to help the children develop proper tooth-brushing habits.

Further, adults as well as children can monitor their tooth-brushing habits over a long period of time using a method of providing guide information according to the present invention. In this way, it is possible to help adults keep their teeth healthy. In addition, information on monitored tooth-brushing may be provided to a third party and utilized as medical information.

DESCRIPTION OF THE DRAWINGS

FIGS. 4 to 10 are exemplary views for describing an operation in which landmarks of the face are analyzed and a personalized dental model is generated (S1200) in FIG. 2.

DETAILED DESCRIPTION

Figure 1:
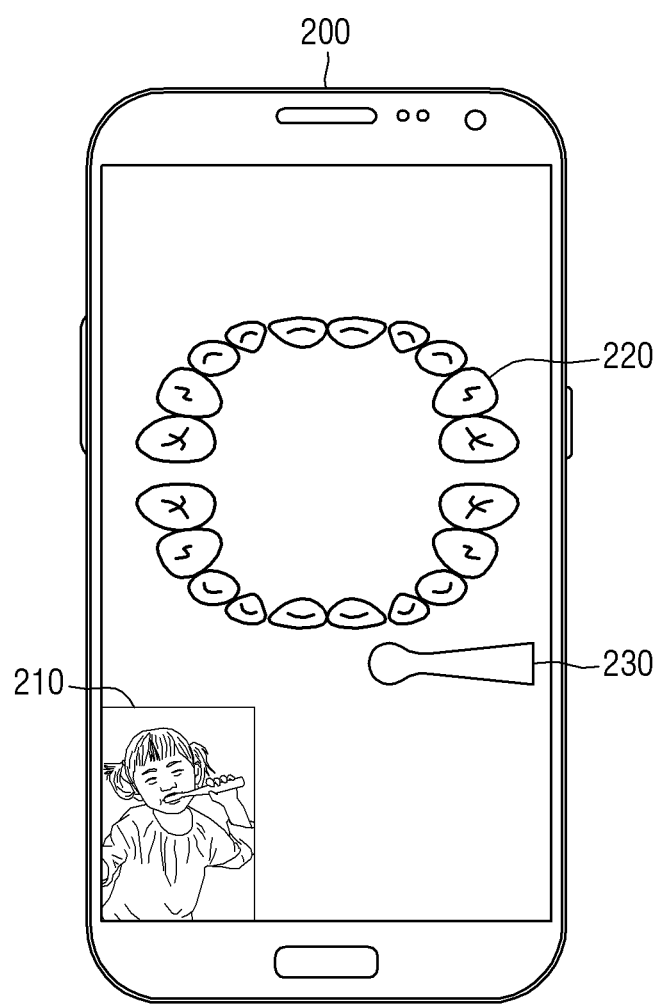
FIG. 1 is a view for describing a method of providing tooth-brushing guide information using augmented reality according to an embodiment of the present invention.

Hereinafter, exemplary embodiments of the present invention will be described in detail with reference to the accompanying drawings. Advantages and features of the present invention and a method of achieving the same should become clear in regard to embodiments described in detail below with reference to the accompanying drawings. However, the present invention is not limited to embodiments disclosed below and may be realized in various other forms. The present embodiments merely make the disclosure of the present invention complete and are provided to completely inform one of ordinary skill in the art to which the present invention pertains of the scope of the invention. The present invention is defined only by the scope of the claims. Like reference numerals refer to like elements throughout.

Unless otherwise defined, all terms including technical or scientific terms used herein have the same meaning as commonly understood by one of ordinary skill in the art to which the present invention pertains. Terms defined in commonly used dictionaries are not to be construed in an idealized or overly formal sense unless expressly so defined herein. Terms used herein are for describing the embodiments and are not intended to limit the present invention. In the specification, a singular expression includes a plural expression unless the context clearly indicates otherwise.

Hereinafter, some embodiments of the present invention will be described with reference to the drawings.

FIG. 1 is a view for describing a method of providing tooth-brushing guide information using augmented reality according to an embodiment of the present invention.

Referring to FIG. 1, it can be seen that an image 210 of a user who is brushing teeth, a virtual dental image 220 shown using augmented reality, and a virtual toothbrush image 230 shown using augmented reality are displayed on a smartphone 200. The user who is brushing teeth is a child whose permanent teeth have not yet erupted. It can be seen that teeth including ten upper teeth and ten lower teeth are overlaid and displayed using augmented reality on the screen.

In the present invention, a separate apparatus such as the smartphone 200 is required in order to provide tooth-brushing guide information using augmented reality. Such a function can be provided through an application installed in the smartphone 200. However, the example in FIG. 1 is merely provided to assist understanding of the present invention, and apparatuses other than the smartphone 200, such as a tablet, and a wearable device such as a smart watch, which are similar to the smartphone 200, may also provide tooth-brushing guide information using augmented reality.

However, an imaging unit such as a camera and a display unit such as a display are essential for providing tooth-brushing guide information using augmented reality. For example, the present invention may also be applied to a smart mirror which is provided by installing a touchscreen in a bathroom and is configured to capture an image of a user, provide the captured image of the user like a mirror, and further provide other additional functions.

In more detail, the smart mirror may provide information on today's weather, information on today's schedule, or the like on the corner of the screen while the user washes his or her face, may capture an image of the user brushing teeth, and provide tooth-brushing guide information using augmented reality on the basis of the captured image of the user brushing teeth. In this way, the present invention may be implemented using various devices.

The image 210 of the user who is brushing teeth, the virtually-generated dental image 220, and the virtually generated toothbrush image 230 are shown as being separated from each other in FIG. 1, but the dental image 220 and the toothbrush image 230 may also be shown as being overlaid on the user image 210. This will be described in more detail below with reference to FIGS. 11A and 11B.

In some cases, only the virtual dental image 220 and the virtual toothbrush image 230 may be provided while the user image 210 is omitted. In such a case, there is an effect of inducing the user to further concentrate on the virtual dental image 220 and the virtual toothbrush image 230. In addition, it is also possible to provide tooth-brushing guide information by displaying only the virtual toothbrush image 230 using augmented reality while the virtual dental image 220 is also omitted. In this case, there is an effect of inducing the user to only concentrate on the tooth-brushing guide information.

In addition, although all of the ten upper teeth and ten lower teeth are displayed in FIG. 1, when, depending on the user, there is a portion at which a tooth has not yet erupted, the corresponding tooth may be omitted when displaying the dental image 220 using augmented reality. For example, when only front teeth have erupted and back teeth have not yet erupted, five or six teeth may be displayed instead of ten teeth.

When the user brushes his or her teeth, the virtually-generated toothbrush image 230 is displayed as being overlaid on an image of teeth which are currently being brushed. The virtual toothbrush image 230 moves identically to the user's hand moving upward/downward/leftward/rightward while the user brushes teeth.

In comparison to the conventional case in which information on tooth-brushing is provided while fixed content such as a video or a flash animation is played, the present invention may arouse more interest in tooth-brushing due to an interaction in which content changes in accordance with a movement of the user. That is, children may view brushing their teeth as a game.

In order to provide tooth-brushing guide information using augmented reality, in the present invention, an image captured by a camera is analyzed in real time, the face of the user is recognized, and then positions of the mouth and the jawline and the position and size of the face are determined. Then, a dental model is generated according to each user, and then the generated dental model is displayed on the screen using augmented reality.

In this case, the dental model generated for each user is a personalized dental model in which a teeth structure, a teeth size, a tooth-brushing state, and the like are reflected. The personalized dental model helps the user concentrate better on the tooth-brushing guide information. The guide information is also provided by being personalized on the basis of the personalized dental model.

In addition, a sound effect or a visual effect may be additionally played when the virtual dental image 220 or the virtual toothbrush image 230 is shown using augmented reality. The sound effect or visual effect may keep the user interested and help the user concentrate on tooth-brushing. That is, the sound effect or visual effect may help children view brushing their teeth as a pleasant daily habit.

Furthermore, feedback on a result of performing tooth-brushing may be provided upon the end of tooth-brushing. Such feedback information may be provided to the user himself or herself, but may also be provided to the child's parents or a dentist. The feedback information may also be utilized as medical information afterwards.

Figure 2:
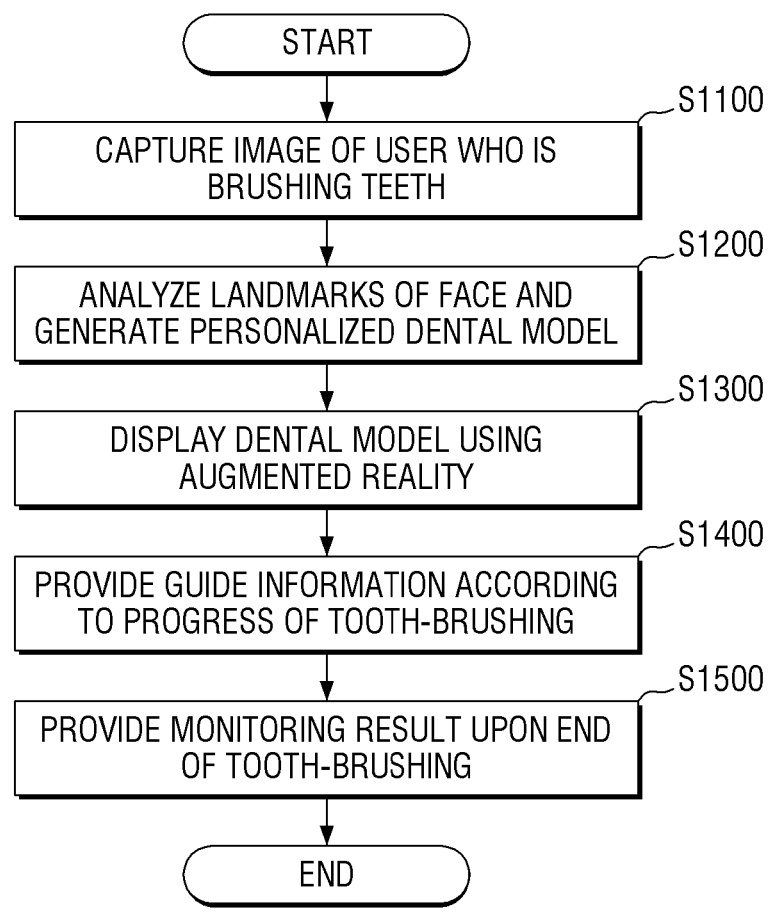
FIG. 2 is a flowchart of the method of providing tooth-brushing guide information using augmented reality according to the embodiment of the present invention.

FIG. 2 is a flowchart of the method of providing tooth-brushing guide information using augmented reality according to the embodiment of the present invention.

Referring to FIG. 2, first, a user who is brushing teeth is captured through a camera of a smartphone 200 (S1100). For this, preferably, a mounting stand capable of mounting the smartphone 200 on a front portion of a washstand or on a mirror is generally installed in a bathroom.

To brush teeth, a child carries the smartphone 200 to the bathroom, mounts the smartphone on the mounting stand, and runs an application. Then, when the child holds a toothbrush and toothpaste and brushes teeth, an image of the child is captured by the camera of the smartphone 200, and the captured image is analyzed.

Landmarks such as eyes, nose, mouth, and ears are identified from the face through the image analysis, the position, structure, or the like of teeth is determined on the basis of the identified landmarks, and a personalized dental model is generated (S1200). That is, in the present invention, virtual dental images 220 which differ for each user are displayed on the screen.

The generated dental model is displayed together with the captured image using augmented reality (S1300). In this case, the dental image 220 may be shown as being overlaid on the captured image 210, or to display the dental image in more detail, the captured image 210 may be displayed as a small thumbnail and the virtual dental image 220 may be shown in larger size as illustrated in FIG. 1.

In this case, the virtual dental image 220 displayed on the screen may be rotated or tilted corresponding to the user turning the head or tilting the head, thereby offering a sense of reality. For this, image processing techniques such as face recognition and pattern recognition may be utilized.

When the user brushes teeth, accordingly, a virtual toothbrush image 230 is displayed together with the captured image 210 and the virtual dental image 220 using augmented reality, and guide information is additionally provided together (S1400). The guide information may be information guiding a degree to which tooth-brushing has been performed on each portion of teeth. Alternatively, the guide information may be information guiding a speed, direction, or the like of tooth-brushing. Alternatively, the guide information may be information guiding a portion which requires more tooth-brushing.

When the user finishes brushing his or her teeth, a monitoring result is provided as feedback (S1500). The end of tooth-brushing may also be determined through the image analysis. For example, through the image analysis, it may be determined that the user has finished brushing his or her teeth when the user puts his or her toothbrush down. Alternatively, the end of tooth-brushing may be determined through a user input as in a method in which the user touches a tooth-brushing done button.

As the monitoring result, information on the degree of how well tooth-brushing has been performed on each portion of the teeth may be provided by being visualized using colors, graphs, or the like. In addition to displaying the feedback information on the smartphone 200, the feedback information may be sent to terminals of designated users, such as the child's parents or a dentist.

The method of providing tooth-brushing guide information using augmented reality proposed by the present invention has been described above. The reason for providing tooth-brushing guide information using augmented reality in the present invention is to arouse the user's interest through an interaction. When the user brushes teeth, since the teeth are inside the mouth, the teeth are invisible even if an image of the user who is brushing teeth is captured using the camera. Thus, the teeth are shown by being virtually visualized, thereby helping the user develop proper tooth-brushing habits.

However, since the teeth are invisible during tooth-brushing in reality, the face of the user should be recognized by analyzing the captured image, and the virtual dental image 220 should be shown in real time on the basis of anatomical information which is based on the landmarks Like this, in the present invention, a personalized dental model is generated using image processing techniques and anatomical analysis to apply augmented reality.

Figure 3:
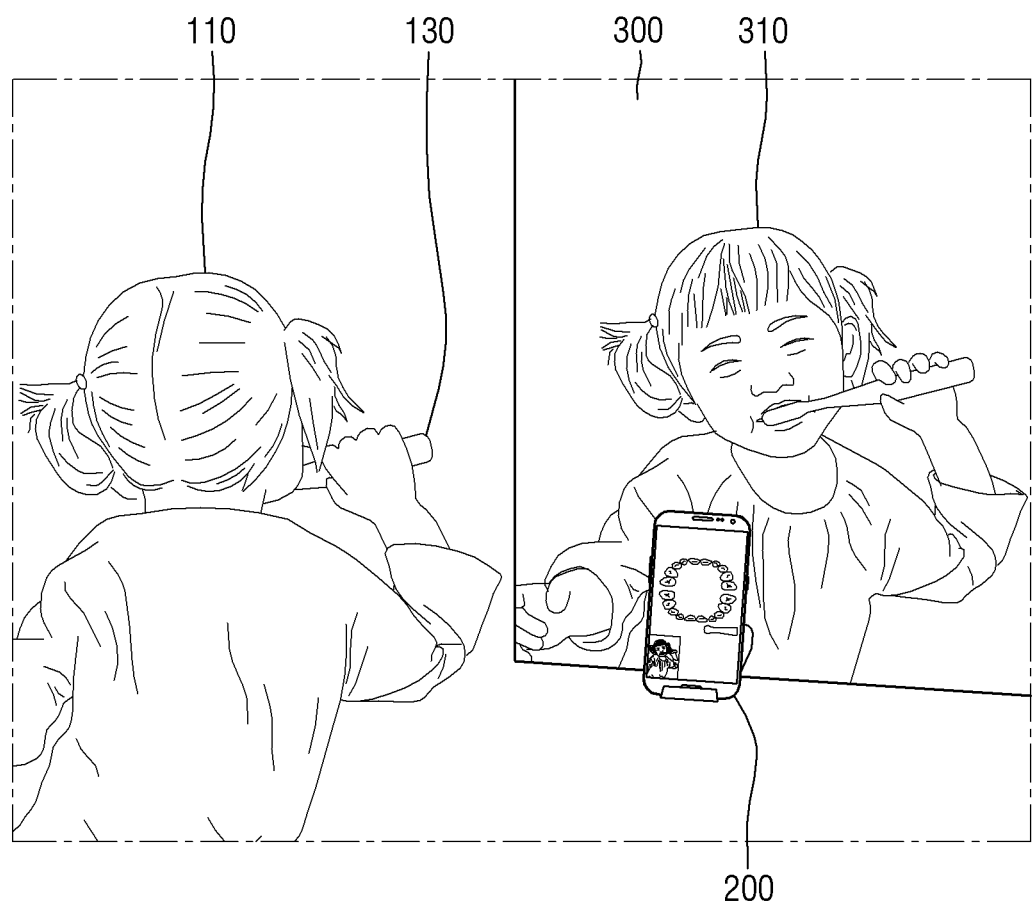
FIG. 3 is an exemplary view for describing an operation in which an image of a user who is brushing teeth is captured (S1100) in FIG. 2.

FIG. 3 is an exemplary view for describing an operation in which an image of a user who is brushing teeth is captured (S1100) in FIG. 2.

Referring to FIG. 3, it can be seen that a smartphone 200 is mounted on a mirror 300 in a bathroom. When a user 110 brushes teeth in reality while holding a toothbrush 130, generally, the user 110 brushes teeth while looking at himself or herself 310 reflected in the mirror 300. However, the user's image 310 in the mirror simply reflects the user 110 realistically, and thus children generally are not very interested therein.

In this case, when tooth-brushing guide information is visually or aurally provided to the user while the user interacts therewith through the smartphone 200 attached on the mirror 300, it is possible to arouse children's interest. In this way, it is possible to help children form proper tooth-brushing habits from the time when deciduous teeth begin to erupt.

FIGS. 4 to 10 are exemplary views for describing an operation in which landmarks of the face are analyzed and a personalized dental model is generated (S1200) in FIG. 2.

Figure 4:
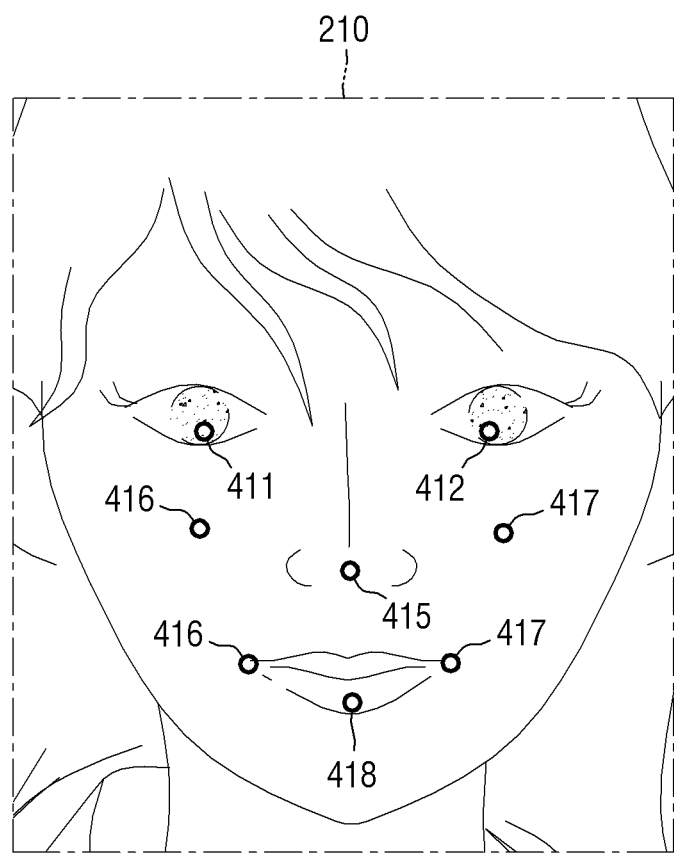

Referring to FIG. 4, examples of facial parts that may be utilized as landmarks in a captured user image 210 are shown. For example, both eyes 411 and 412, both cheeks 413 and 414, nose 415, mouth corners 416 and 417, center of mouth 418, and the like may be utilized as landmarks. Through analysis of such landmarks, information such as the position or size of teeth may be estimated even when the user brushes his or her teeth with closed lips.

Figure 5A:
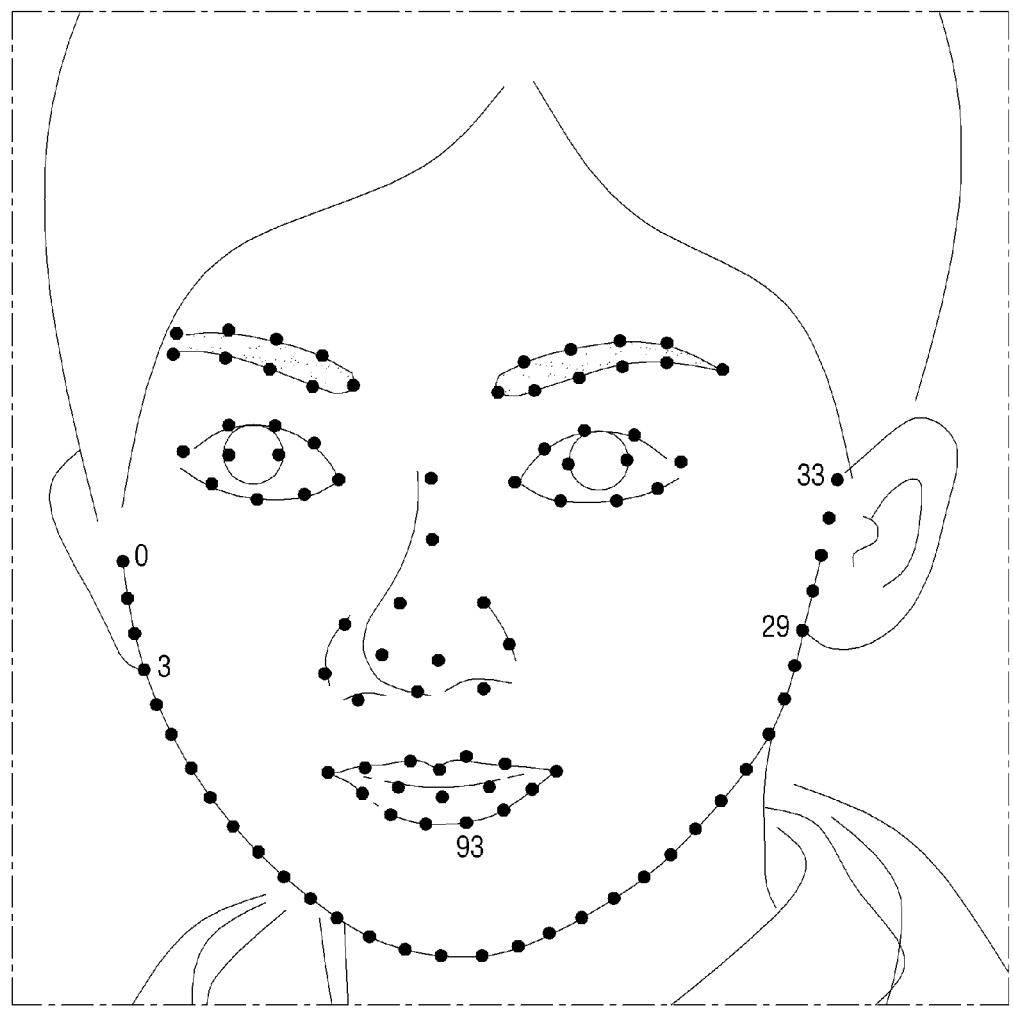

Referring to FIG. 5A, it can be seen that a wider variety of landmarks have been numbered according to each position. The present invention estimates information on invisible teeth by combining anatomical information with such landmarks.

For example, take a close look at position number 3 and position number 29, which are points at which both ears meet the jawline. Generally, these positions correspond to ends of the mandible. Also, position number 93, which is the center of the mouth, is an area where front teeth are located.

Figure 5B:
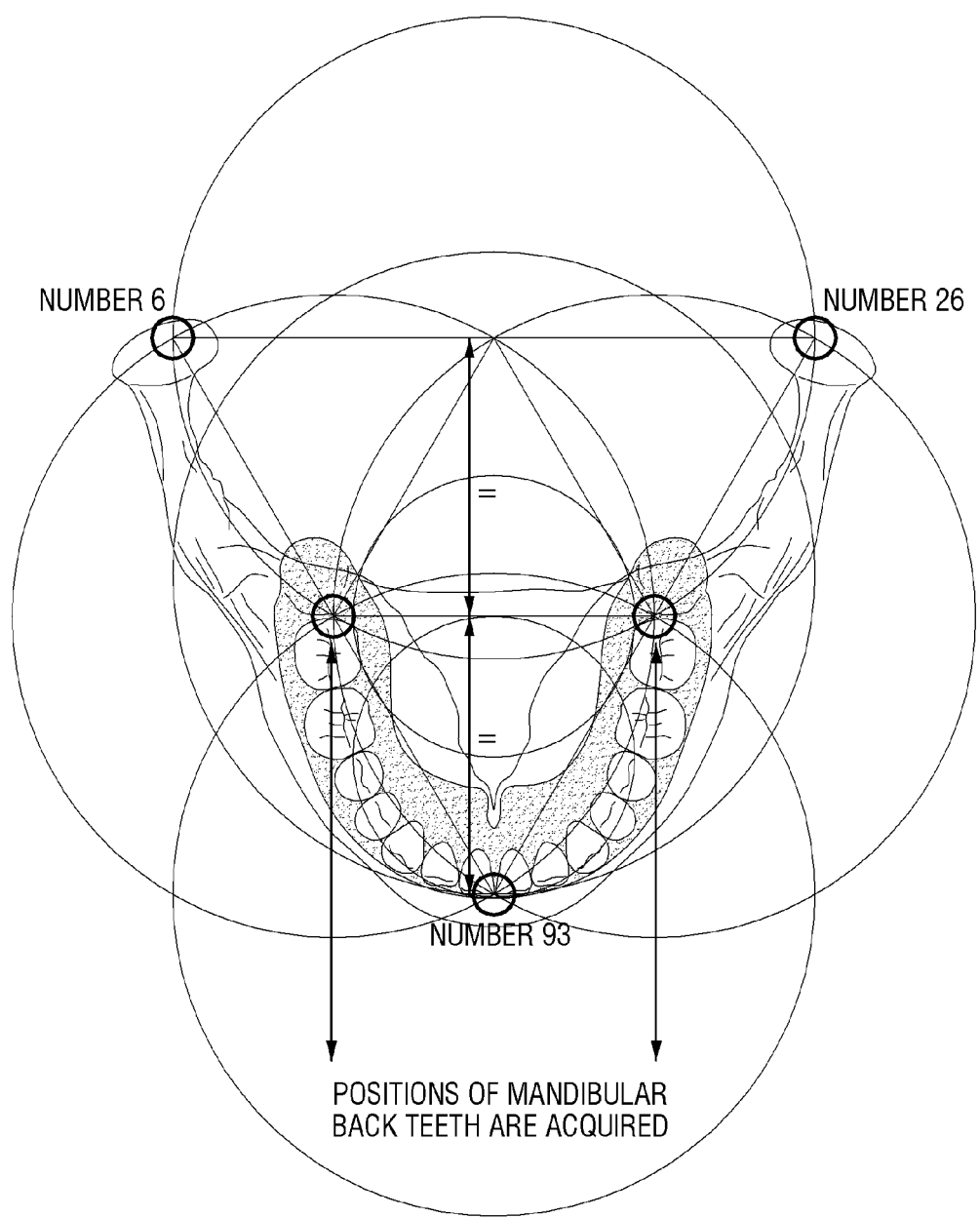

Then, as can been seen in FIG. 5B, it can be estimated that mandibular left back teeth are located in between position number 3 and position number 93. Likewise, it can be estimated that mandibular right back teeth are located in between position number 29 and position number 93.

Not only the position of teeth, but also the size of the jaw of the user may be calculated on the basis of the jawline ranging from position number 0 to position number 33, and the size of teeth may be estimated on the basis of the calculated size of the jaw. Since the size of teeth increases as the size of the jaw becomes larger, the size of teeth may also be estimated in consideration thereof.

Figure 5C:
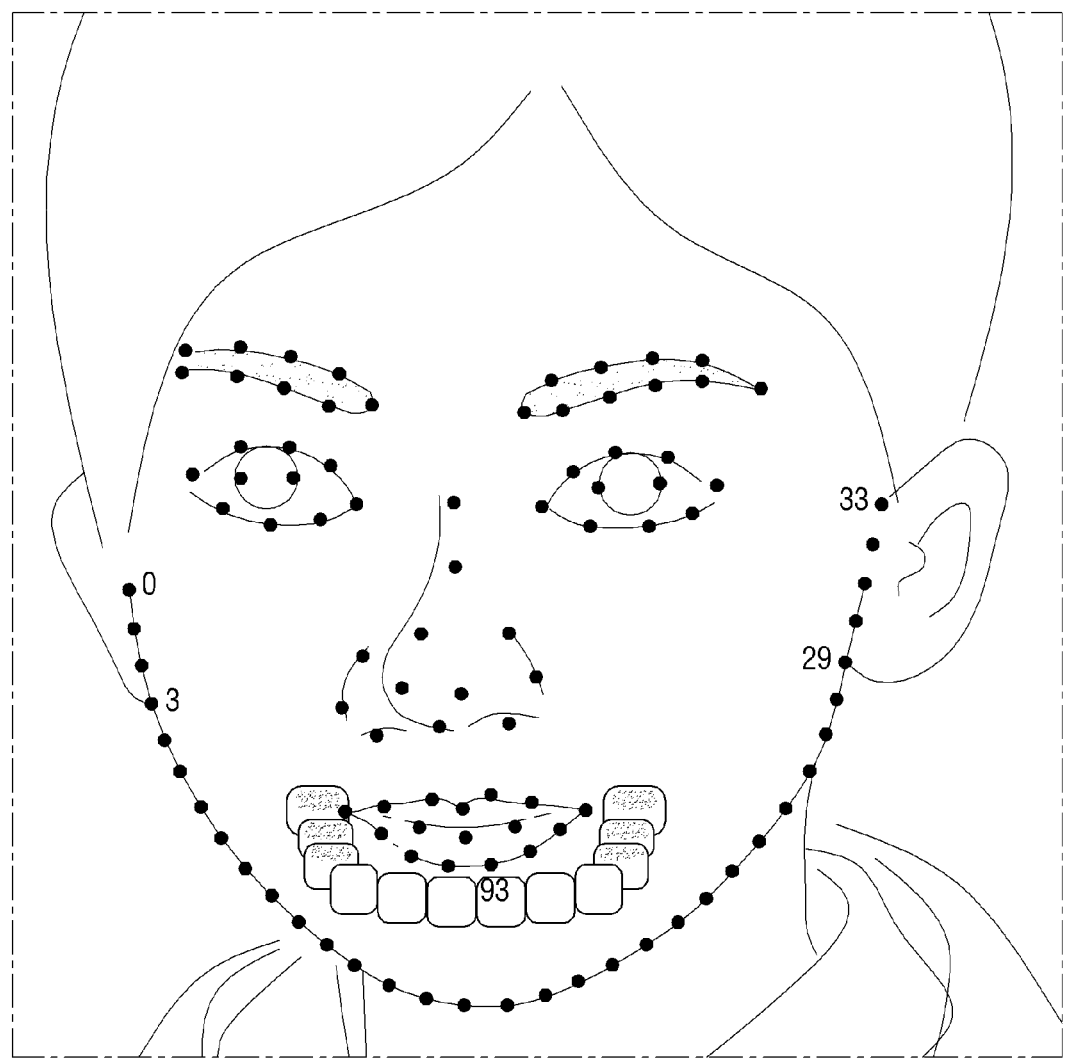

Referring to FIG. 5C, it can be seen that a personalized dental model of the user is displayed with a virtual dental image as an overlay on the screen. In addition to the position and size of teeth, the number of teeth or the like may be personalized and shown. Particularly, in the case of children, since the number of teeth varies according to whether the teeth are deciduous teeth or permanent teeth, this may be reflected in a dental model.

As described above with reference to FIGS. 5A to 5C, in the present invention, the position, size, and the like of teeth of the user may be estimated using anatomical information. A result of the estimation is referred to as a personalized dental model. However, this is merely an example for describing the process of generating a dental model using anatomical information, and various other pieces of information may be further used.

For example, the size or position of teeth generally have correlation with the age, gender, height, weight, and the like of the user. Such pieces of information may be additionally input by the user and be utilized in generating a personalized dental model.

Furthermore, by guiding the user to separately take a picture with his or her mouth open while saying "Ahhhhh" in the process of user registration in the application of the smartphone 200, a dental image may be directly captured and utilized in generating a personalized dental model.

Other than the above, an X-ray image, a computerized tomography (CT) image, or the like may be received through communication with a server of a dental office regularly visited by the corresponding user, and the received image may be analyzed and utilized in generating a personalized dental model. In comparison to an ordinary picture, a medical image is more appropriate for generating an accurate dental model.

Figure 6:
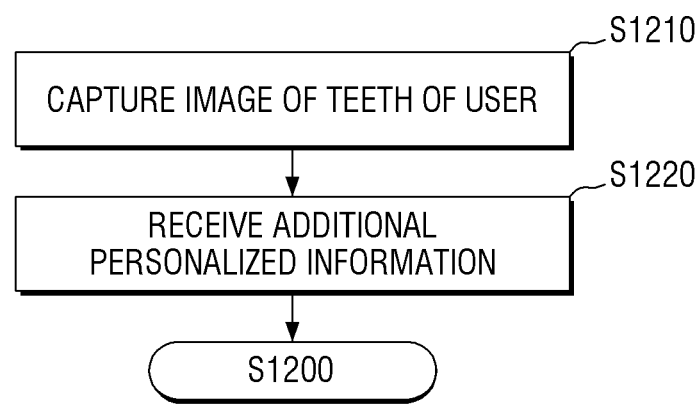

Referring to FIG. 6, prior to the operation in which the personalized dental model is generated (S1200), an operation in which an image of teeth of the user is captured (S1210) or an operation in which additional information is received from the user (S1220) may be further performed. Although operation S1210 and operation S1220 are shown as sequential operations in FIG. 6, operations S1210 and S1220 may also be simultaneously performed or performed in reverse, and only one of the operations may be performed.

Landmarks may be extracted from a captured image of a user's face, and the position, size, or the like of teeth may be estimated by combining anatomical information with the extracted landmarks, but it is difficult to obtain further information. For example, there is limitation in obtaining information on the number of teeth, whether areas from which teeth have been extracted are present, whether decayed teeth are present, and the like even when anatomical information is used.

Of course the age or the like of the user may be estimated by analyzing a facial image, and whether teeth are deciduous teeth or permanent teeth may be estimated. However, this too is limited information. To supplement the information, personal information such as the date of birth, gender, and age may be further received from the user.

Figure 7:
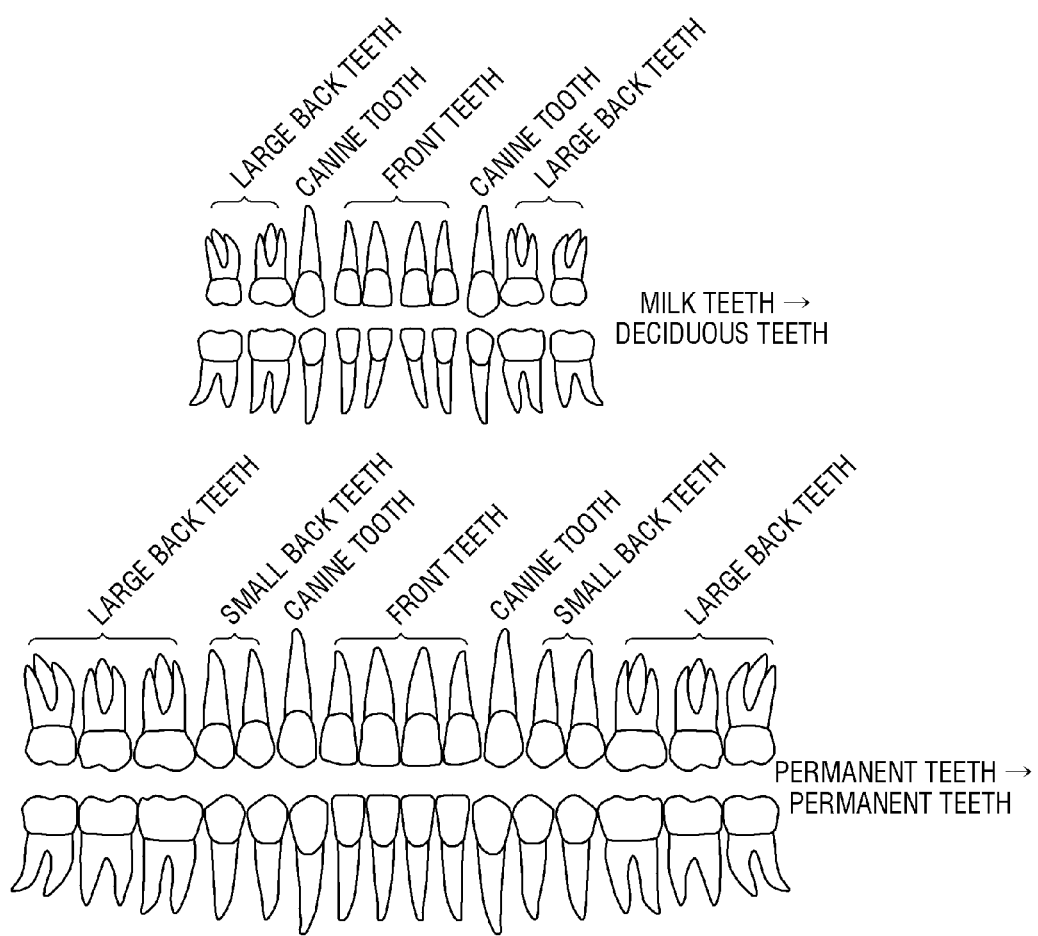

Referring to FIG. 7, differences between deciduous teeth and permanent teeth can be seen. Teeth that first develop in humans are referred to as deciduous teeth. These teeth are also referred to as milk teeth. The teeth are referred to as milk teeth due to erupting during infancy. The deciduous teeth erupt 6 to 7 months after birth and grow until 20 to 30 months. In the case of deciduous teeth, only deciduous molars are present regardless of the type of molars.

Deciduous incisors refer to a total of eight teeth grown at the foremost part of the jaw. Among the eight teeth, four teeth are grown at the upper jaw while the remaining four teeth are grown at the lower jaw, and for both the upper jaw and the lower jaw, two teeth are present at each of left and right parts. The four teeth at the center are referred to as deciduous central incisors while the four teeth which are present further outward are referred to as deciduous lateral incisors. The size of the deciduous lateral incisors is smaller than the size of the deciduous central incisors. The deciduous central incisors and the deciduous lateral incisors erupt 6 to 8 months after birth.

Deciduous canines refer to teeth present further outward than the deciduous lateral incisors. A total of four deciduous canines are present. The deciduous canines erupt 16 to 20 months after birth.

Deciduous molars refer to teeth present further outward than the deciduous canines. A total of eight deciduous molars are present. Teeth present inward are referred to as first deciduous molars while teeth present further outward are referred to as second deciduous molars. The first deciduous molars do not resemble any of the permanent teeth. Although the first deciduous molars have three roots like molars, the appearance of the first deciduous molars are closer to that of premolars. The second deciduous molars resemble first molars among the permanent teeth. The first deciduous molars and the second deciduous molars erupt 12 to 13 months after birth.

In contrast to the deciduous teeth, teeth that erupt after the deciduous teeth fall out are referred to as permanent teeth.

Incisors refer to a total of eight teeth present at the foremost part. The incisors erupt from the exact areas from which the deciduous incisors have fallen out. Since the size of the incisors is greater than the size of the deciduous incisors, the deciduous incisors erupt in a spaced manner, and the incisors fill the spaces as they grow. If spaces between the deciduous incisors are insufficient, the incisors may overlap with each other, erupt in a misaligned manner, or become protruding teeth. The incisors serve to incise food, play an important role in terms of aesthetics, and are essential in pronunciation. The incisors at the center are referred to as central incisors while the incisors present further outward are referred to as lateral incisors.

Canines refer to four teeth present further outward than the incisors. Due to having a sharp central portion in comparison to the incisors, the canines are commonly referred to as canine teeth. The canines serve to tear food and play a very important role in terms of aesthetics. This is because the canines are prominent in an arch formed by teeth. Due to having the longest root length among teeth, the canines have high durability. This is because the canines initially come into contact with each other in the process of chewing food and guides paths along which the jaws move. When the canines wear or fall out, a method of chewing food changes.

Premolars are eight teeth present further outward than the canines and are commonly referred to as small back teeth. Premolars closer to the center are referred to as first premolars while premolars present further outward than the first premolars are referred to as second premolars. The premolars serve to break food into pieces. From the premolars, there are two or more cusps. All of the maxillary premolars have two cusps, but mandibular second premolars sometimes exhibit a three-cusp form in which there are two tongue-side cusps.

Molars refer to twelve teeth present at the outermost part. From the center toward the end, molars are sequentially referred to as first molars, second molars, and third molars in that order, and the third molars are commonly referred to as wisdom teeth. The molars serve to crush and grind food. Maxillary molars often have four cusps and three roots while mandibular molars often have five cusps and two roots. A fifth small cusp may be formed at the tongue side of the maxillary first molars, and the maxillary second molars may be formed as if having three cusps due to degeneration of an outer cusp at the tongue side. The mandibular first molars have four cusps disposed roughly in a square form and another cusp attached outside. The form of the mandibular second molars is also similar, but the mandibular second molars often exhibit a four-cusp form in which the fifth cusp attached outside is degenerated. The mandibular third molars have various forms. The mandibular third molars are sometimes well-developed and have a form similar to that of the mandibular first molars but may also be smaller than the mandibular second molars which are degenerated and reduced in size.

As can be seen in FIG. 7, the size and shape of teeth vary according to whether the teeth are deciduous teeth or permanent teeth. Also, the total number of teeth varies. Thus, the user may have a greater sense of reality when whether the user has deciduous teeth or permanent teeth is distinguished and displayed using augmented reality. However, there is limitation in estimating such information from a captured image of the face. Thus, the date of birth may be additionally received from the user and utilized.

FIG. 8A is a view in which times when deciduous teeth erupt and times when the deciduous teeth fall out are summarized in a table. Referring to FIG. 8A, maxillary first front teeth (=deciduous central incisors) erupt between 7 to 8 months and fall out between the age of 6 to 7 years. Maxillary second front teeth (=deciduous lateral incisors) erupt between 8 to 9 months and fall out between the age of 7 to 8 years. Maxillary canine teeth (=deciduous canines) erupt between 16 to 20 months and fall out between the age of 10 to 12 years. Maxillary first back teeth (=first deciduous molars) erupt between 12 to 16 months and fall out between the age of 9 to 11 years. Maxillary second back teeth (=second deciduous molars) erupt between 20 to 30 months and fall out between the age of 10 to 12 years.

Referring to FIG. 8A, mandibular first front teeth (=deciduous central incisors) erupt between 6 to 7 months and fall out between the age of 6 to 7 years. Mandibular second front teeth (=deciduous lateral incisors) erupt between 6 to 7 months and fall out between the age of 7 to 8 years. Mandibular canine teeth (=deciduous canines) erupt between 16 to 20 months and fall out between the age of 9 to 12 years. Mandibular first back teeth (=first deciduous molars) erupt between 12 to 16 months and fall out between the age of 9 to 11 years. Mandibular second back teeth (=second deciduous molars) erupt between 20 to 30 months and fall out between the age of 10 to 12 years.

Referring to FIG. 8B, times when permanent teeth erupt may be confirmed for maxilla and mandible. Since permanent teeth do not naturally fall out unless special circumstances occur, only eruption times are summarized for permanent teeth.

Referring to FIG. 8B, maxillary first front teeth (=central incisors) erupt between the age of 7 to 8 years, and mandibular first front teeth erupt between the age of 6 to 7 years. Maxillary second front teeth (=lateral incisors) erupt between the age of 8 to 9 years, and mandibular second front teeth (=lateral incisors) erupt between the age of 7 to 8 years. Maxillary canine teeth (=canines) erupt between the age of 11 to 12 years, and mandibular canine teeth (=canines) erupt between the age of 9 to 10 years.

Maxillary first small back teeth (=first premolars) erupt between the age of 10 to 11 years, and mandibular first small back teeth (=first premolars) erupt between the age of 10 to 12 years. Maxillary second small back teeth (=second premolars) erupt between the age of 10 to 12 years, and mandibular second small back teeth (=second premolars) erupt between the age of 10 to 12 years.

Maxillary first large back teeth (=first molars) erupt between the age of 6 to 7 years, and mandibular first large back teeth (=first molars) erupt between the age of 6 to 7 years. Maxillary second large back teeth (=second molars) erupt between the age of 12 to 13 years, and mandibular second large back teeth (=second molars) erupt between the age of 11 to 13 years. Maxillary third large back teeth (=third molars) erupt between the age of 17 to 21 years, and mandibular third large back teeth (=third molars) erupt between the age of 17 to 21 years.

Like this, even the same types of deciduous teeth differ in terms of eruption times and fall-out times according to the positions thereof. Eruption times and fall-out times of front teeth differ according to whether the front teeth are maxillary or mandibular. The number of teeth varies according to whether the teeth are deciduous teeth or permanent teeth.

Thus, upon receiving the date of birth from the user, whether the teeth are deciduous teeth or permanent teeth may be distinguished by counting back the number of months and number of years from the received date of birth, and even if the teeth are deciduous teeth, erupted teeth and unerupted teeth may be distinguished. In this way, a more accurate personalized dental model may be generated, and the generated personalized dental model may be shown using augmented reality.

The method of providing tooth-brushing guide information using augmented reality that the present invention provides may be provided through an application or the like of the smartphone 200. In this process, a user profile may be generated. A tooth-brushing situation may be continuously monitored on the basis of the generated user profile, and feedback may be given. Here, in the process in which the user profile is generated, pieces of information such as the date of birth, gender, height, weight, number of teeth, position of teeth, number of decayed teeth, and position of decayed teeth may be received.

Also, in the process in which the profile is generated, the picture taken with the mouth open may be received, and pieces of information such as whether decayed teeth are present or the like may be reflected to the personalized dental model. Pieces of information such as areas from which teeth have erupted, areas from which teeth have fallen out, and areas in which decayed teeth are present may be reflected in generating personalized guide information.

For example, guide information may be generated in a customized manner such that areas from which teeth have fallen out are omitted from the tooth-brushing guide information or areas in which decayed teeth are present are guided to be brushed more for a longer period of time. That is, personalized guide information may be generated on the basis of the personalized dental model.

Figure 9A:
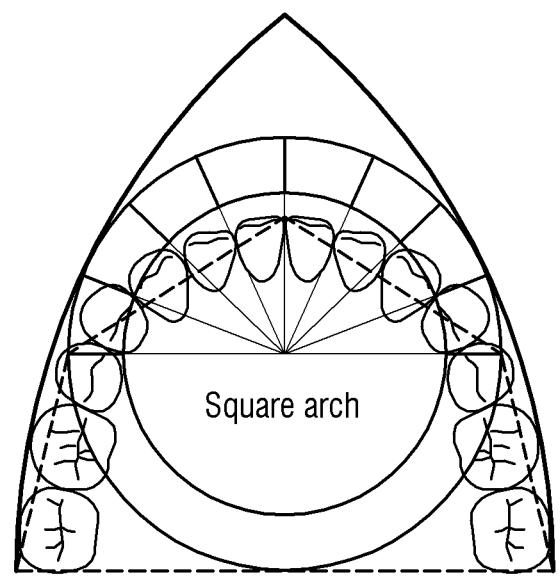
Figure 9B:
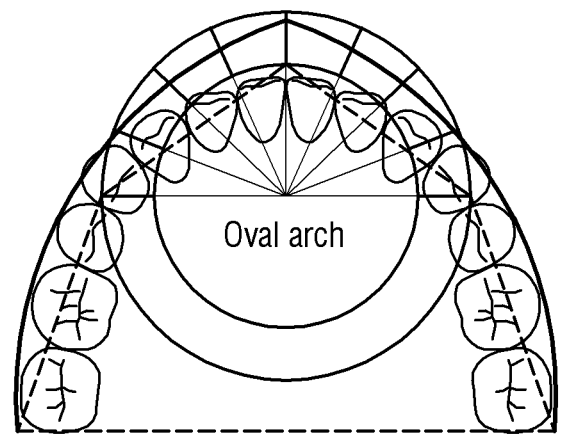
Figure 9C:
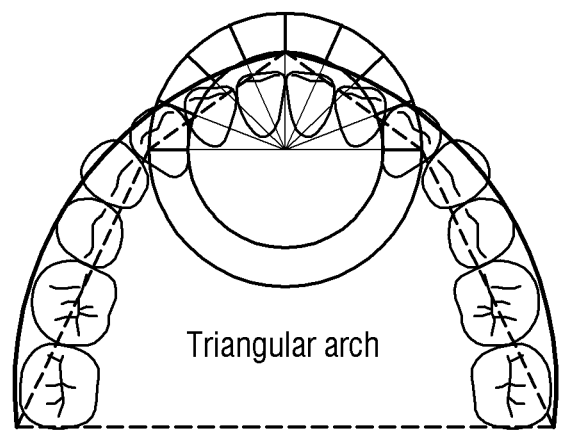

The arrangement of teeth may be further reflected in the process in which a personalized dental model, to which the position, size, number, and the like of teeth are reflected, is generated on the basis of anatomical information and information received from the user. FIGS. 9A to 9C illustrate examples of arrangement of teeth.

FIG. 9A illustrates a square arch. FIG. 9B illustrates an oval arch. FIG. 9C illustrates a triangular arch. The arrangement of teeth is mainly classified into a square form, an oval form, and a triangular form on the basis of an angle formed between a line of back teeth and a line of front teeth.

According to a 2010 statistic, the oval form was the most common at 44%, followed by the square form at 30% and the triangular form at 26%. As a result of comparison according to age, the oval form accounted for 48%, the square form accounted for 28%, and the triangular form accounted for 24% in people younger than 20; the oval form accounted for 42%, the square form accounted for 31%, and the triangular form accounted for 27% in people in their 20s; and the oval form accounted for 40%, the square form accounted for 35%, and the triangular form accounted for 25% in people in their 30s. Like this, the oval form accounted for a large portion in the age group of 30s or younger. In contrast, the square form accounted for 35%, the triangular form accounted for 34%, and the oval form accounted for 31% in people in their 40s. The square arch accounted for a large portion and the oval arch accounted for a smaller portion in comparison to the younger age group. This showed that the arch form of Koreans was becoming westernized.

Like this, the arch forms also exhibit different characteristics according to age. Particularly, since the arch form is closely related to the jawline, the arch form may be estimated from anatomical information of the jawline.

Figure 10:
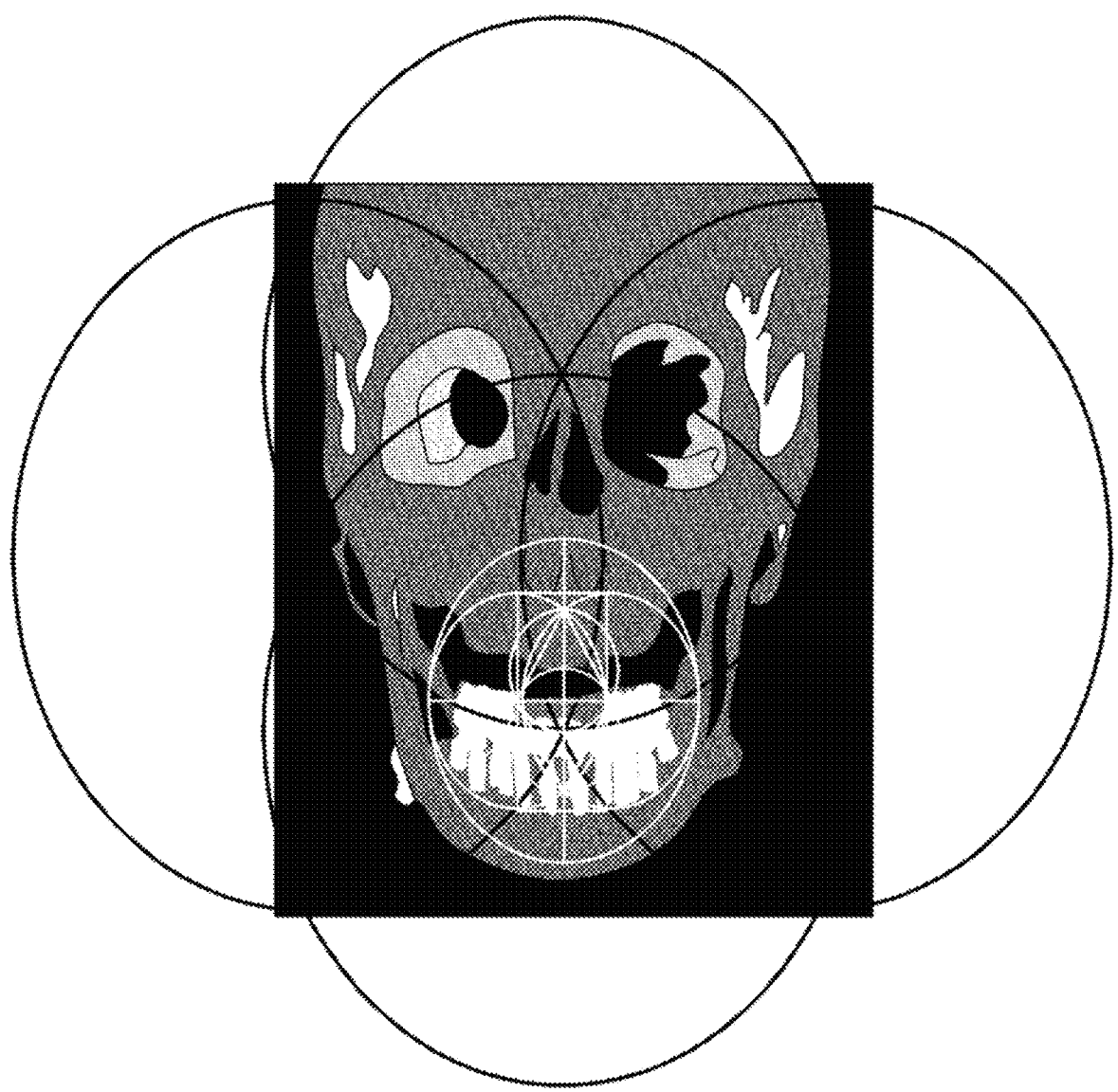

Also, when generating a personalized dental model as illustrated in FIG. 10, an X-ray image or the like may be received from a server of a dental office regularly visited by the corresponding user, and a more accurate dental model may be generated on the basis of the received X-ray image or the like. In the case of children, a more accurate dental model may be generated in association with a dental office since children need continuous dental care, and personalized guide information may be provided on the basis of the generated dental model.

Particularly, opinions of one's regular dentist may be reflected when generating guide information. For example, a weighted value may be assigned to each area when guide information is generated by reflecting an opinion of one's regular dentist that a specific area be more intensively brushed.

Figure 11A:
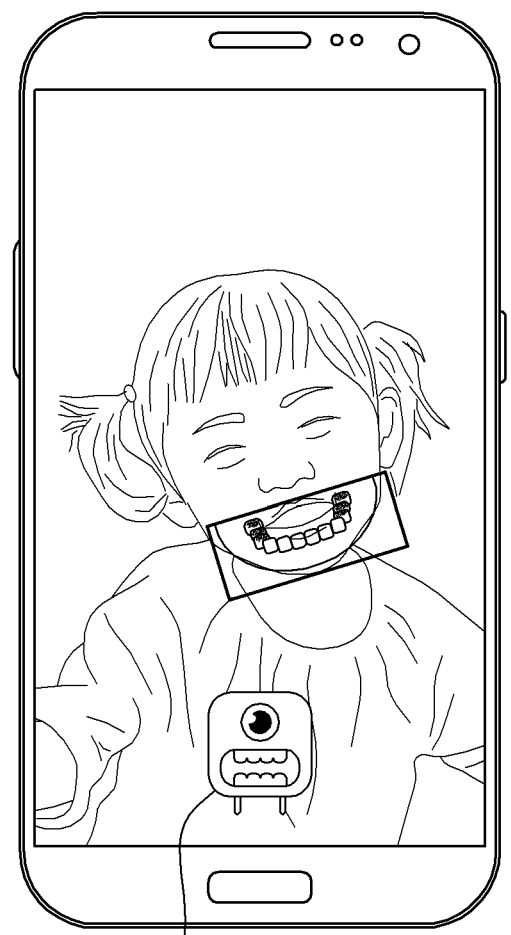
FIGS. 11A and 11B are exemplary views for describing an operation in which the dental model is displayed using augmented reality (S1300) in FIG. 2.
Figure 11B:
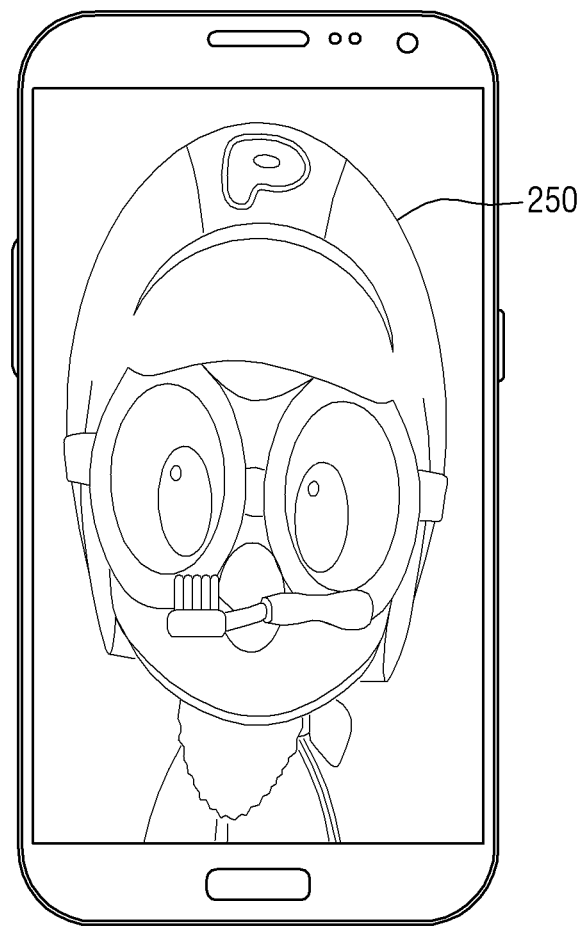

FIGS. 11A and 11B are exemplary views for describing the operation in which the dental model is displayed using augmented reality (S1300) in FIG. 2.

Referring to FIG. 11A, it can be seen that a virtual dental image 220 is displayed as being overlaid on a captured image of a user. By showing the virtual dental image 220 using augmented reality even while the user's mouth is closed, changes in the state of teeth may be visualized and shown during the process in which the user brushes teeth.

Particularly, as can be seen in FIG. 11A, when the user tilts his or her head to the right, the position of teeth is also shown as being tilted accordingly. Since augmented reality is used, the position of teeth may be estimated by combining anatomical information with the contour of the face, the jawline, and the like of the user, and a personalized dental model may be displayed on the corresponding position.

In this way, tooth-brushing guide information, which has a greater sense of reality in comparison to a method in which tooth-brushing is performed while simply looking in the mirror or a method in which tooth-brushing is performed while watching video content that is simply played without any interaction, may be provided to the user.

Also, an image other than the virtual dental image 220 and the virtual toothbrush image 230 may be shown together using augmented reality. In FIG. 11A, it can be seen that the tooth-brushing process is combined with a game, and a game character image 240 is displayed together.

In FIG. 11B, it can be seen that the user image is displayed by being replaced with a Pororo image 250 using augmented reality. Although the entire user image is replaced with the Pororo image 250 in FIG. 11, the user image may also be partially replaced with the Pororo image 250 instead of being entirely replaced therewith. For example, only Pororo's glasses and hat may be composed with the user image 210, and a result may be shown using augmented reality. When characters that children love in addition to Pororo are realized using augmented reality and states in which the characters brush their teeth are shown, tooth-brushing may be considered to be a pleasant game by children.

Only the Pororo image 250 is illustrated in FIG. 11B, but images of various other characters may also be used. Particularly, since such character images have copyrights, licenses may be received through contracts, and the character images may be sold through an application. In this way, profit may be gained by charging fees for some functions of the application.

Figure 12:
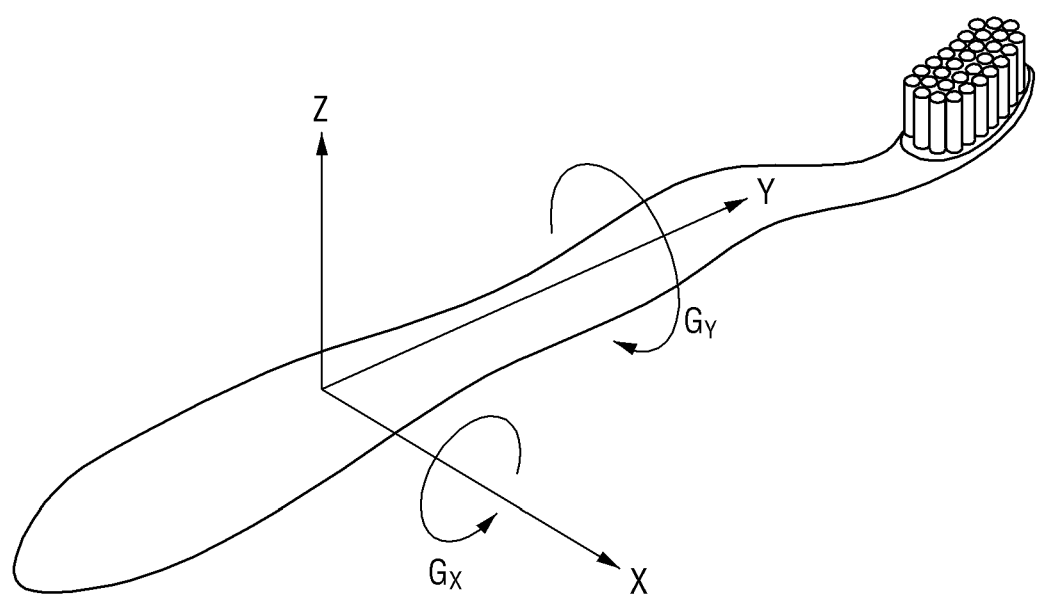
FIG. 12 is an exemplary view for describing an operation in which guide information is provided according to the progress of tooth-brushing (S1400) in FIG. 2.

FIG. 12 is an exemplary view for describing the operation in which guide information is provided according to the progress of tooth-brushing (S1400) in FIG. 2.

Guide information may include tooth-brushing progress information in which teeth are divided in to predetermined areas and the degree to which tooth-brushing is performed on each area is displayed using colors or the like. For example, in the mandible, left back teeth may be set as a first area, front teeth may be set as a second area, and right back teeth may be set as a third area, and three parts including the front, top, and back surfaces of the first area, two parts including the front and back surfaces of the second area, and three parts including the top and back surfaces of the third area, which constitute a total of eight parts, may be shown using colors.

As tooth-brushing is performed, guide information may be provided to the user by changing colors of the eight parts to red, yellow, and yellow-green in that order so that tooth-brushing is evenly performed throughout all areas. In this way, a habit of brushing only specific areas may be corrected.

Also, guide information may include information that guides areas that require tooth-brushing. For example, tooth-brushing may be combined with a game, and bacteria may be shown as being overlaid on teeth in a specific area using augmented reality. The screen may be configured such that, when the user brushes the corresponding area, the corresponding bacteria is eliminated with a visual effect and a sound effect and a score is obtained. In addition to the bacterial image, a visualized image of food scraps may be shown using augmented reality.

Then, a child may be induced to evenly brush all the teeth simply by brushing parts on which bacteria or food scraps appear. In this process, the game may be configured such that bacteria appear more frequently on areas in which decayed teeth are present and bacteria do not appear on areas in which teeth are not present. Through the customized guide information, it is possible to help children develop proper tooth-brushing habits.

In addition, guide information may include information that guides the direction, speed, and the like of tooth-brushing. The virtual toothbrush image 230 shown on the screen using augmented reality may be displayed using a method in which, when the user brushes teeth, the virtual toothbrush image 230 moves corresponding thereto, but, in addition, guide information may be displayed before the user begins to brush teeth.

For example, a state in which the virtual toothbrush image vertically brushes the front teeth may be displayed with a voice guidance saying "Let's brush front teeth three times." An image of a child who is brushing teeth may be captured, and through image analysis, voice feedback saying "Well done!" may be provided when the child brushes teeth according to guide information.

In addition, guide information through the virtual toothbrush image 230 may be shown in different ways in consideration of the age and fine motor development status of the user. For example, horizontal tooth-brushing techniques (=roll technique, Fones technique), which are relatively easy, may be mainly guided for users who are 3 to 8 years old while vertical tooth-brushing techniques (=Bass technique, modified Bass technique), which are relatively complicated, may be mainly guided for users who are 8 years old or older.

In this case, an actual tooth-brushing process of the child may be determined using a direction of movement, a distance of the movement, and the like through image analysis. However, in addition, as illustrated in FIG. 12, a three-axis acceleration sensor may be built in a toothbrush such that information on movement of the toothbrush is received by the smartphone 200 via wireless communication and analyzed, thereby determining the actual tooth-brushing process of the child.

Referring to FIG. 12, a direction from a toothbrush handle to a toothbrush head may be defined as the y-axis, a direction parallel to toothbrush bristles may be defined as the z-axis, and the remaining axis orthogonal to the y-axis and the z-axis may be defined as the x-axis. A tooth-brushing direction may be determined by collecting information on rotation in the x-axis direction and rotation in the y-axis direction in addition to information on movement in each of the x-axis, y-axis, and z-axis directions.

In this case, the direction in which the user holds the toothbrush may be determined, and the direction of the toothbrush and areas of teeth on which tooth-brushing is being performed may be determined according to whether the user is right-handed or left-handed. Also, an angle of the virtual toothbrush image 230 may be determined by calculating an angle between the user's hand holding the toothbrush and a main body of the toothbrush.

In this case, various communication methods such as wireless fidelity (Wi-Fi) communication, Bluetooth communication, ZigBee communication, third generation (3G) communication, long term evolution (LTE) communication, and near-field communication (NFC) may be used as a method of communication between the toothbrush and the smartphone 200. That is, any communication method that performs communication using wireless signals may be applied.

In addition to being visually or aurally provided using the smartphone 200, guide information may be tactilely provided via the toothbrush. For example, when the user follows the direction of the toothbrush, the number of times of tooth-brushing, and duration of tooth-brushing exactly as displayed on the screen of the smartphone 200, a control signal may be transmitted from the smartphone 200 to the toothbrush so that the toothbrush vibrates, and the toothbrush may receive the control signal and provide feedback to the user through vibration. Conversely, when the user follows guide information poorly, feedback may be provided by causing a haptic effect in the toothbrush.

Guide information may be displayed on the screen by various other means using augmented reality. For example, the virtual toothbrush image 230 is placed in an area that has to be brushed by the user, and a virtual effect (bubble of toothpaste, change in color of teeth, asterisk, and the like) is placed in an area currently being brushed by the user. Guide information may be configured such that, when the two areas match, the virtual toothbrush image 230 disappears.

The smartphone 200 may display the remaining battery of the toothbrush through communication with the toothbrush, and when the battery of the toothbrush has to be replaced, the smartphone 200 may provide information that guides the replacement to the user in advance. In addition, the smartphone 200 may analyze the degree of wear of the toothbrush through image analysis or the like, and when the toothbrush has to be replaced, the smartphone 200 may provide information that advises of the replacement to the user in advance.

In addition, upon the end of tooth-brushing, a virtual cup image may be displayed using augmented reality so as to visually provide guide information on rinsing the mouth to the user. In addition, when toothpaste remains around the mouth after tooth-brushing is finished, the remaining toothpaste may be detected through image analysis, and information that guides the user to wash areas around the mouth may be provided to the user.

In addition, a background of the user may be changed to a virtual space other than a bathroom such as the beach, school, or playground using augmented reality so that the user feels as if he or she is brushing teeth in an unusual space. In this way, it is possible to continuously arouse interest of children who easily get bored.

The above-described method of providing guide information using augmented reality may also be utilized when providing medical information. For example, although explanation is given using an X-ray image when showing decayed teeth in dental offices conventionally, from now on, decayed teeth may be displayed by virtual teeth being overlaid on the face reflected on the screen.

The application of the method of providing guide information using augmented reality may be extended to body parts other than teeth. For example, in a pediatric office instead of a dental office, when an explanation on influenza is given to a child, the stages of influenza may be explained by generating a virtual bronchial image and showing the generated image by overlaying the generated image on an image of the child other than using an X-ray image or the like. When the child gets an influenza shot with such an explanation, the child may be induced to consider visiting the pediatric office and getting a shot as a hospital role play and not have any fear about visiting the pediatric office and getting a shot.

Like this, a personalized body part model may be generated for various body parts using anatomical information, and when content related to the generated model is provided while the generated model is displayed using augmented reality, there is an effect in that the user's degree of understanding and level of concentration related to the corresponding content are increased.

In addition, when the user touches the dental image 230 shown on the screen using augmented reality, educational content such as functions of the corresponding teeth and whether teeth are permanent teeth may be further displayed on the screen. In addition, the user's oral cavity state (whether orthodontic treatment has been performed, whether teeth whitening has been performed, whether areas from which teeth have been extracted are present, the size and number of teeth, etc.) may be analyzed, and pieces of information on toothbrushes or toothpastes may be provided. In this way, profit may be gained by utilizing the provided pieces of information as advertisements or the like.

In addition, instead of only the same image being used as the virtual toothbrush image 230, the color and size of the toothbrush may be changed according to the age, gender, height, and weight which are predicted through facial recognition or input by the user. A character toothbrush image 230 may be displayed on the screen for children.

Figure 13:
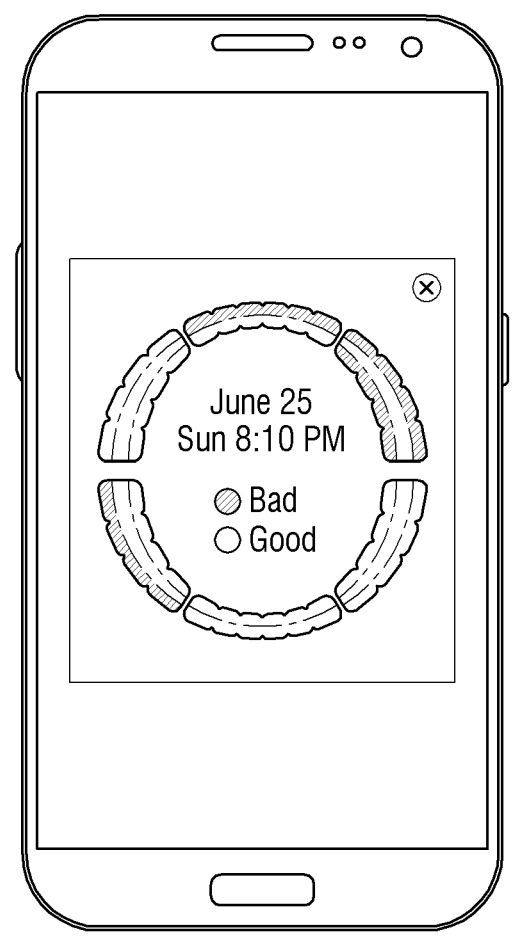
FIG. 13 is an exemplary view for describing an operation in which a monitoring result is provided upon the end of tooth-brushing (S1500) in FIG. 2.

FIG. 13 is an exemplary view for describing the operation in which a monitoring result is provided upon the end of tooth-brushing (S1500) in FIG. 2.

Referring to FIG. 13, it can be seen that a result of monitoring tooth-brushing performed on Sunday, Jun. 25, 2017 8:10 pm is displayed. As described above, in the mandible, left back teeth may be set as a first area, front teeth may be set as a second area, and right back teeth may be set as a third area, and three parts including the front, top, and back surfaces of the first area, two parts including the front and back surfaces of the second area, and three parts including the top and back surfaces of the third area, which constitute a total of eight parts, may be shown using colors.

Even in the case of the maxilla, likewise, a total of eight parts are displayed. Areas where tooth-brushing has been performed well may be indicated by white color, and areas where the number of times of tooth-brushing, time during which tooth-brushing is performed, or the like is insufficient may be indicated by yellow color so that a result of tooth-brushing is intuitively shown to the user.

When the user still has deciduous teeth, the mandible may be displayed by being divided into two left and right areas instead of three areas, thereby simply showing a monitoring result. As described above, since the horizontal tooth-brushing methods (=roll method, Fones method) are guided according to age for children, a tooth-brushing result may also be displayed by being divided into a total of four parts including, to the left and right, an inner part, and an outer part at the left and an inner part and an outer part at the right.

While the total of eight parts with respect to the mandible may be provided as a monitoring result when the user has permanent teeth, a monitoring result may be provided by being simplified to a total of four parts with respect to the mandible for children who have deciduous teeth.

However, this is merely an example for assisting in understanding of the invention, and a tooth-brushing result may be provided by dividing teeth into a certain number of areas in various other ways and subdividing each area into a certain number of parts. In addition, a monitoring result may be provided for each tooth without dividing the teeth into a certain number of areas. Furthermore, a monitoring result may be provided by also dividing each tooth and portions between teeth into a certain number of areas.

In addition, although only a result of one tooth-brushing is displayed in FIG. 13, several tooth-brushing results may be accumulated, and a tooth-brushing result over a number of days may be shown using colors, or the degree to which each tooth-brushing has been performed may be converted to a score and the scores may be provided in the form of a graph. In addition to showing a tooth-brushing result simply by using colors, a monitoring result which is given aurally such as a voice message saying "Your lower back teeth may be decayed if you keep brushing teeth like this" may be provided together.

Figure 14:
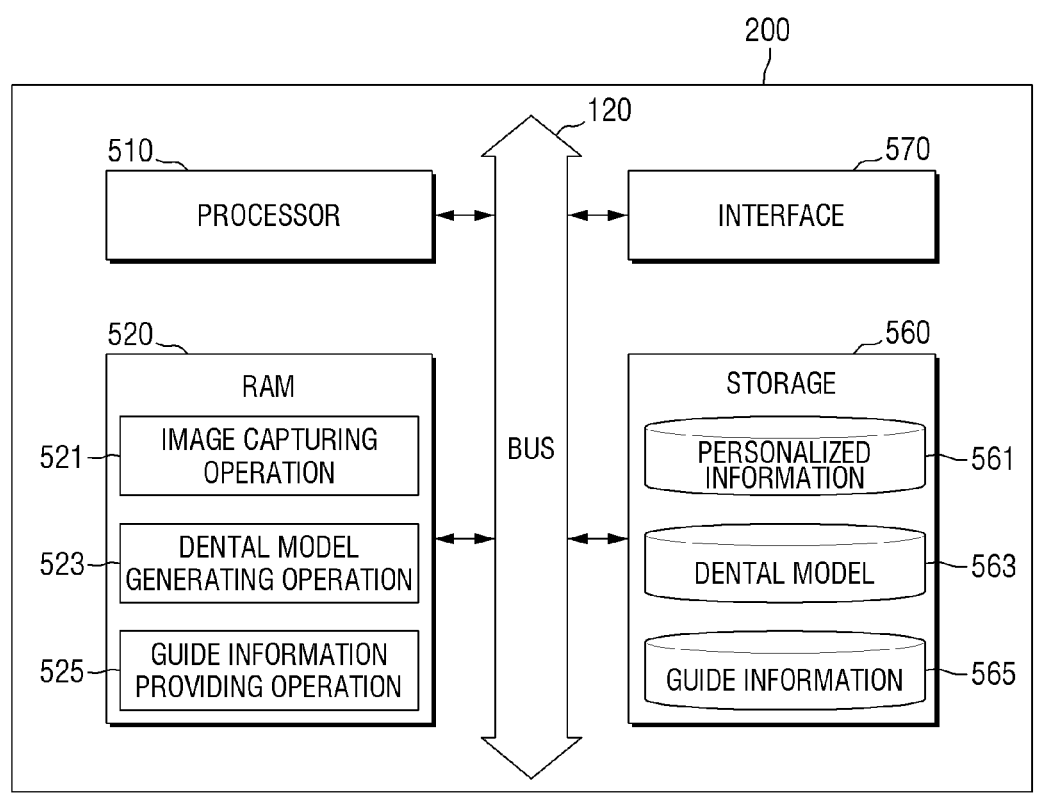
FIG. 14 is a hardware configuration diagram of an apparatus for providing tooth-brushing guide information using augmented reality according to an embodiment of the present invention.

FIG. 14 is a hardware configuration diagram of an apparatus for providing tooth-brushing guide information using augmented reality according to an embodiment of the present invention.

Referring to FIG. 14, a tooth-brushing guide information providing apparatus 200 may include one or more processors 510, a memory 520, a storage 560, and an interface 570. The processor 510, the memory 520, the storage 560, and the interface 570 transmit and receive data to and from each other via a system bus 550.

The processor 510 executes a computer program loaded in the memory 520, and the memory loads the computer program in the storage 560. The computer program may include an image capturing operation 521, a dental model generating operation 523, and a guide information providing operation 525.

The image capturing operation 521 captures an image of a user, who is about to brush his or her teeth, using a camera (not illustrated). In this case, preferably, an image of the upper half of the body of the user including the face is captured. It is an object of the present invention to analyze the image captured by the image capturing operation 521 in real time and provide a personalized dental model and personalized guide information to the corresponding image.

For this, the dental model generating operation 523 analyzes the captured image. After the face is initially detected, the contour of the face, landmarks of the face, and the like are identified, and the position, size, and arrangement of teeth are estimated using anatomical information.

With reference to personalized information 561 stored in the storage 560, secondly, whether teeth are permanent teeth, whether decayed teeth are present, the number of teeth, the color of teeth, and the like are reflected in generating a personalized dental model, and the generated dental model is stored as a dental model 563 in the storage 560 via the system bus 550.

The personalized information used in this case is information received in advance from the user via the interface 570. The personalized information includes the date of birth, gender, height, weight, and the like of the user. In addition, the personalized information may include a dental image directly captured by the user, a dental X-ray image received from a server of a dental office, and the like.

As described above, the personalized dental model 563 includes pieces of information such as the position, size, and arrangement of teeth, whether the teeth are permanent teeth, whether decayed teeth are present, the number of teeth, and the number of decayed teeth, and the like. In this way, virtual dental images which differ for each user may be displayed on the screen using augmented reality.

The guide information providing operation 525 provides personalized guide information 56 that corresponds to the previously-generated personalized dental model 563 while providing the captured image to the user. The personalized guide information 563 may include the degree to which tooth-brushing has been performed according to dental conditions of each individual and feedback information on the direction, number of times, duration, and the like of tooth-brushing.

Each element in FIG. 14 may be software or hardware, such as a field programmable gate array (FPGA) and an application-specific integrated circuit (ASIC). However, the elements are not limited to being meant as software or hardware. The elements may be configured to be in an addressable storage medium or configured to execute one or more processors. Functions provided within the elements may be implemented by further subdivided elements or implemented by a single element that performs a specific function by combining a plurality of elements.

The above-described methods according to embodiments of the present invention may be performed by execution of a computer program implemented with computer readable codes. The computer program may be sent from a first computing apparatus to a second computing apparatus via a network, such as the Internet, and installed in the second computing apparatus so that the computer program is used in the second computing apparatus. The first computing apparatus and the second computing apparatus include any of a server apparatus, a physical server that belongs to a server pool for a cloud service, and a fixed type computing apparatus such as a desktop personal computer (PC).

The computer program may be a program stored in a recording medium such as a digital versatile disk (DVD)-read only memory (ROM) and a flash memory device.

The embodiments of the present invention have been described above with reference to the accompanying drawings, but those of ordinary skill in the art to which the present invention pertains should understand that the present invention may be practiced in other specific forms without changing the technical idea or essential features thereof. Therefore, the above-described embodiments are illustrative in all aspects and should not be understood as limiting.

It is claimed:

1. A method of providing tooth-brushing guide information using augmented reality on a smartphone in wireless communication with a toothbrush, the method comprising:
    the smartphone analyzing a captured image of a user, recognizing a face of the user, and identifying landmarks of the face;
    the smartphone generating a dental model of the user using the landmarks;
    the smartphone receiving toothbrush movement information by wireless communication from the toothbrush, the movement information including three-axis acceleration information captured by the toothbrush while the user is brushing
    the smartphone providing a virtual dental image by augmented reality on a screen of the smartphone using the dental model including
        analyzing the captured image and estimating a hand of the user with which a toothbrush is held and an angle thereof, and
        displaying on the screen of the smartphone a position and an angle of a virtual toothbrush image by augmented reality on the basis of the estimated hand and angle thereof and the movement information; and
    the smartphone providing tooth-brushing guide information while the tooth-brushing is in progress using the dental model and the movement information, including the smartphone dividing the dental model into a predetermined number of parts,
        the smartphone visually or aurally guiding one or more of the number of required tooth-brushing strokes, a direction of tooth-brushing, and duration of tooth-brushing for each part,
        the smartphone displaying on the screen of the smartphone a degree to which tooth-brushing is performed on each part using colors.

2. The method of claim 1, wherein the identifying of the landmarks of the face includes identifying one or more of an eyebrow, an eye, a nose, both cheeks, a mouth, an ear, and a jawline of the user as the landmarks.

3. The method of claim 1, wherein the generating of the dental model of the user includes estimating one or more of a position, a size, and an arrangement of teeth of the user using the landmarks.

4. The method of claim 3, wherein the estimating of one or more of a position, a size, and an arrangement of the teeth of the user includes:
    estimating that mandibular right back teeth are located at a first midpoint portion between a first position at which a jawline and a right ear of the user meet and a position of the center of a mouth of the user;
    estimating that mandibular left back teeth are located at a second midpoint portion between a second position at which the jawline and a left ear of the user meet and the position of the center of the mouth of the user; and
    estimating that front teeth are located at the position of the center of the mouth of the user.

5. The method of claim 3, wherein the estimating of one or more of a position, a size, and an arrangement of the teeth of the user includes:
    estimating a size of the jaw of the user from a jawline of the user; and
    estimating the size of the teeth of the user using the estimated size of the jaw.

6. The method of claim 3, wherein the estimating of one or more of a position, a size, and an arrangement of the teeth of the user includes:
    estimating a shape of a jaw of the user from a jawline of the user; and
    estimating the arrangement of the teeth of the user as any one of a square arch, an oval arch, and a triangular arch using the estimated shape of the jaw.

7. The method of claim 1, wherein the generating of the dental model of the user includes:
    receiving personalized information including one or more of a date of birth, a gender, a height, a weight, a number of teeth, a position of teeth, a number of decayed teeth, and position of decayed teeth from the user; and
    modifying the dental model of the user using the received personalized information.

8. The method of claim 7, wherein the modifying of the dental model of the user includes:
    counting back a number of months and number of years from a date of birth of the user and determining whether the teeth of the user are permanent teeth on the basis of the counted number of months and number of years; and
    limiting the number of teeth included in the dental model to 20 or less when the teeth of the user are deciduous teeth and to 28 or less when the teeth of the user are permanent teeth.

9. The method of claim 7, wherein the modifying of the dental model of the user includes:
    counting back the number of months and number of years from the date of birth of the user and determining whether the teeth of the user are the permanent teeth on the basis of the counted number of months and number of years; and modifying one or more of the size and shape of the teeth included in the dental model according to a result of determining whether the teeth of the user are permanent teeth.

10. The method of claim 7, wherein the modifying of the dental model of the user includes modifying one or more of the number, size, and shape of the teeth included in the dental model using one or more of the gender, height, age, and weight of the user.

11. The method of claim 1, wherein the providing of the virtual dental image by augmented reality includes:

when a first tooth has not yet erupted or has fallen out in the dental model, not displaying a tooth at a position corresponding to the first tooth in the virtual dental image.

12. The method of claim 1, wherein the providing of the virtual dental image by augmented reality includes further providing a virtual toothbrush image by augmented reality or providing only the virtual toothbrush image instead of providing the virtual dental image.

13. The method of claim 1, wherein the displaying of the degree to which tooth-brushing is performed on each part using colors includes, when the teeth of the user are deciduous teeth, dividing the dental model into a total of eight parts including front and back surfaces of maxillary left teeth, front and back surfaces of mandibular left teeth, front and back surfaces of maxillary right teeth, and front and back surfaces of mandibular right teeth.

14. The method of claim 1, wherein the displaying of the degree to which tooth-brushing is performed on each part using colors includes, when the teeth of the user are permanent teeth, dividing the dental model into a total of sixteen parts including front, top, and back surfaces of maxillary left back teeth, front, top, and back surfaces of mandibular left back teeth, front and back surfaces of maxillary front teeth, front and back surfaces of mandibular front teeth, front, top, and back surfaces of maxillary right back teeth, and front, top, and back surfaces of mandibular right back teeth.

15. The method of claim 1, wherein the providing of the tooth-brushing guide information includes dividing the dental model into a predetermined number of parts and visually or aurally guiding one or more of the number of required tooth-brushing strokes, a direction of tooth-brushing, and duration of tooth-brushing for each part.

16. The method of claim 15, wherein the visually or aurally guiding of one or more of the number of required tooth-brushing strokes, the direction of tooth-brushing, and the duration of tooth-brushing for each part includes, when a first tooth has not yet erupted or has fallen out in the dental model, not guiding for a position corresponding to the first tooth.

17. The method of claim 15, wherein the visually or aurally guiding of one or more of the number of required tooth-brushing strokes, the direction of tooth-brushing, and the duration of tooth-brushing for each part includes guiding horizontal tooth-brushing using a roll technique or a Fones technique when the user is younger than a predetermined age and guiding vertical tooth-brushing using a Bass technique or a modified Bass technique in other cases.

* * * * *